US008567951B2

(12) United States Patent
Huang et al.

(10) Patent No.: US 8,567,951 B2
(45) Date of Patent: Oct. 29, 2013

(54) CHARACTERIZATION OF RETINAL PARAMETERS BY CIRCULAR PROFILE ANALYSIS

(75) Inventors: Yijun Huang, Pleasantville, NY (US); Tetsuyoshi Royama, Montvale, NJ (US); Alexandre Kotchkin, Ridgewood, NJ (US)

(73) Assignee: Topcon Medical Systems, Inc., Oakland, NJ (US)

( * ) Notice: Subject to any disclaimer, the term of this patent is extended or adjusted under 35 U.S.C. 154(b) by 238 days.

(21) Appl. No.: 13/224,568

(22) Filed: Sep. 2, 2011

(65) Prior Publication Data

US 2012/0002170 A1 Jan. 5, 2012

Related U.S. Application Data

(62) Division of application No. 12/465,724, filed on May 14, 2009, now Pat. No. 8,025,407.

(51) Int. Cl.
*A61B 3/00* (2006.01)

(52) U.S. Cl.
USPC ........................................................ 351/246

(58) Field of Classification Search
USPC .................. 351/206, 246, 205, 207, 221, 200
See application file for complete search history.

(56) References Cited

U.S. PATENT DOCUMENTS 8,256,897 B2 * 9/2012 Huang et al. .................. 351/206

* cited by examiner

*Primary Examiner* — Hung Dang
(74) *Attorney, Agent, or Firm* — Wolff & Samson, PC

(57) ABSTRACT

Certain diseases of the retina are diagnosed by circular profile analysis of retinal parameters, such as thickness. Retinal thickness around a user-defined circle on the retina is measured by three-dimensional optical coherence tomography or other ophthalmological techniques. Abnormally thin regions are identified by comparing a measured function of thickness vs. polar angle to a reference function of thickness vs. polar angle. A degree of abnormality is characterized by the ratio of the integral of the measured thickness function to the integral of the reference thickness function over the abnormally thin region, as specified by a range of polar angles.

31 Claims, 11 Drawing Sheets

US 8,567,951 B2

CHARACTERIZATION OF RETINAL PARAMETERS BY CIRCULAR PROFILE ANALYSIS

CROSS-REFERENCE TO RELATED APPLICATION

This application is a divisional of prior U.S. patent application Ser. No. 12/465,724, filed on May 14, 2009, which is herein incorporated by reference in its entirety.

This application is related to U.S. patent application Ser. No. 12/465,750, filed May 14, 2009, now U.S. Pat. No 8,025,407 and published as U.S. Patent Application Publication No. 2010/0290005 on Nov. 18, 2010 entitled Circular Profile Mapping and Display of Retinal Parameters, which is herein incorporated by reference in its entirety.

BACKGROUND OF THE INVENTION

The present invention relates generally to ophthalmic characterization, and more particularly to characterization of a retina by circular profile analysis.

Diagnostics for eye disorders typically include a detailed ophthalmic examination of the retina. For initial examination, an eye doctor will view the retina through an ophthalmoscope. For a permanent record, the retina is typically photographed with a fundus camera. A fundus photograph directly records various anatomical features of the retina, such as the optic disc, fovea, blood vessels, and lesions. The imaging capabilities of fundus photography may be enhanced by supplementary techniques. A high-contrast image of retinal blood vessels, for example, may be photographed after the injection of a fluorescent dye into the bloodstream. The resulting image is referred to as a fluorescein angiogram (FA).

More sophisticated techniques have recently been developed for diagnostics of the eye. One such technique is three-dimensional optical coherence tomography (3-D OCT). In this technique, a light beam is directed onto the retina. Part of the beam is back-reflected, and interferometric analysis of the back-reflected light yields information on the structure of the retina. By varying optical parameters of the light probe, features at different depths below the surface of the retina may be analyzed. With this process, an image of a cross-section of the retina may be generated by scanning the optical probe along a line on the retina. By rastering the optical probe across the surface of the retina, a series of cross-sectional images may be produced. The series of cross-sectional images may be used to characterize the 3-D structure of the retina, and parameters such as local retinal thickness may be measured by 3-D OCT.

Analysis of the thickness of the retina may be used to diagnose certain diseases of the eye, such as glaucoma and diabetic retinopathy. One indication of the health of the eye may be provided by comparing the retinal thickness of the patient's eye with reference data acquired from a population of healthy eyes. Progression of eye disease may also be monitored by measuring changes in retinal thickness over a period of time.

The retinal thickness is dependent on the loci (points on the retina) at which the measurements are made. The measurement loci are specified with respect to a reference point on the retina. Two common reference points are the center of the optic disc and the center of the fovea. One set of historical reference data from a large population of healthy retinas has been acquired with a Zeiss Stratus OCT 3, a commonly used instrument in the field of ophthalmology. This instrument measures the retinal thickness at loci on a circle centered at the center of the optic disc. The radius of the circle is fixed at 1.73 mm.

Thickness data is conventionally displayed on a monitor or printout as a circle divided into equally-sized arcs. For each arc, the average value of the thickness is displayed, and the arc is color coded to indicate a statistical range into which the average value falls. In a conventional display, four color codes are used. Although this simple display allows an eye doctor to rapidly assess the thickness distribution of the retina, there are several shortcomings: (a) The conventional color codes have coarse granularity. There is no mechanism to indicate whether the thickness changes abruptly or gradually from one arc to another. (b) The results are highly variable as a function of the length and orientation of the arcs. There is no mechanism for providing consistent detection of local variations. (c) There is no mechanism for detailed tracking of the growth of retinal defects over time. (d) There is no mechanism for associating anomalous thickness measurements with the presence of blood vessels or other anatomical features.

What are needed are method and apparatus for analyzing, mapping, and displaying retinal parameter measurements.

BRIEF SUMMARY OF THE INVENTION

In an embodiment of the invention, eye disease is diagnosed by characterizing a retinal parameter as a function of a polar angle. A reference parameter function is defined. A measured parameter function is calculated. An interval of polar angles is determined such that the value of the measured parameter function is less than the value of the reference parameter function for all angles within the interval of polar angles. An integral of the reference parameter function over the interval of polar angles is calculated. An integral of the measured parameter function over the interval of polar angles is calculated. A characterization value based at least in part on the integral of the reference parameter function over the interval of polar angles and the integral of the measured parameter function over the interval of polar angles is calculated.

These and other advantages of the invention will be apparent to those of ordinary skill in the art by reference to the following detailed description and the accompanying drawings.

DETAILED DESCRIPTION

Figure 1A:
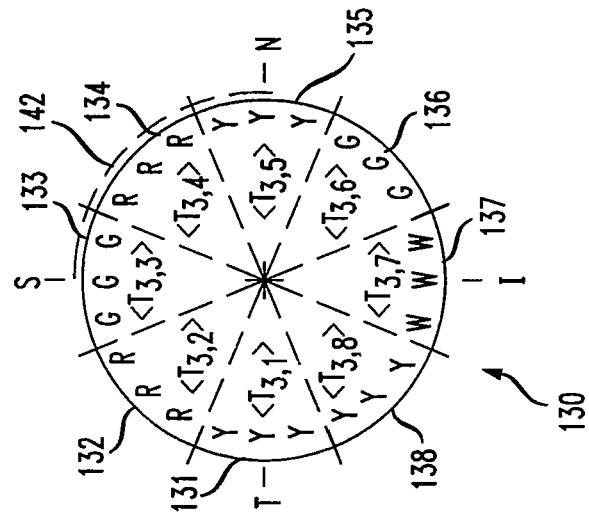
FIG. 1A-FIG. 1C show conventional circle scans of retinal thickness.
Figure 1B:
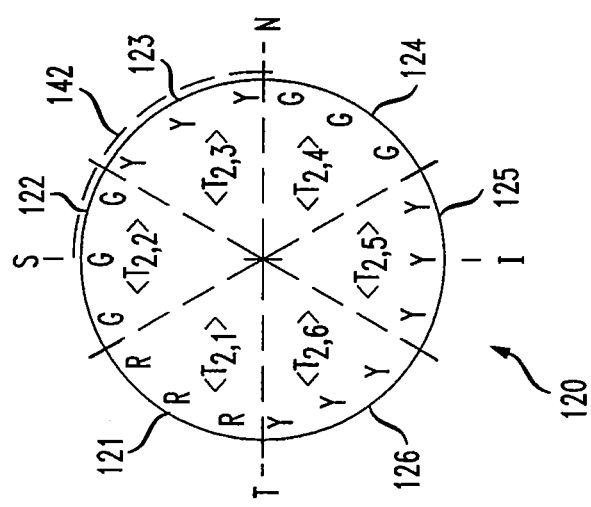
Figure 1C:
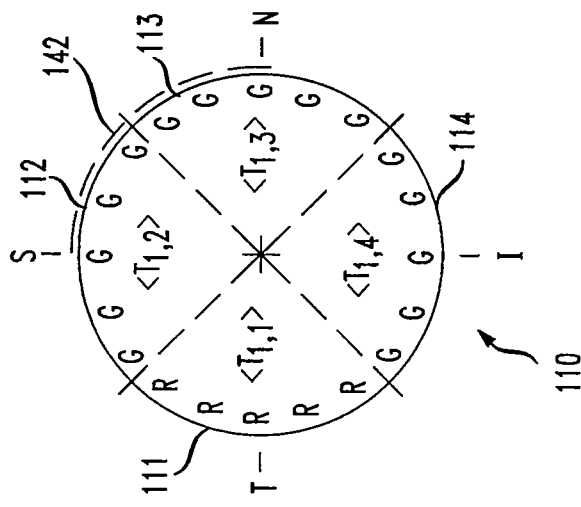

FIG. 1A-FIG. 1C are schematic representations of conventional retinal thickness plots of data (also referred to as circle scans) measured with a Zeiss Stratus OCT 3 or similar ophthalmological instrument. Measurements are taken along a circle with a center at the nominal center of the optic disc and with a radius fixed at 1.73 mm. The angular orientation of measurement loci along the circle are referenced with respect to TSNIT geometry, where T=Temporal, S=Superior, N=Nasal, and I=Inferior. The measurements along the circle are divided into groups defined by arcs. The number and orientation of the arcs are arbitrary and defined by a user (such as an eye doctor). For measurements along each arc, the average thickness <T> is displayed.

In FIG. 1A, plot 110 displays measurements divided into four arcs, arc 111-arc 114. Note that the dashed radial lines are used only to aid demarcation of the arcs in the figures. The measurement loci fall only along the arcs, not in the regions within the circle. The corresponding average thickness along each arc is $<T_{1,1}>$-$<T_{1,4}>$, respectively. In FIG. 1B, plot 120 displays measurements divided into six arcs, arc 121-arc 126. The corresponding average thickness along each arc is $<T_{2,1}>$-$<T_{2,6}>$, respectively. In FIG. 1C, plot 130 displays measurements divided into eight arcs, arc 131-arc 138. The corresponding average thickness along each arc is $<T_{3,1}>$-$<T_{3,8}>$, respectively.

Figure 3A:
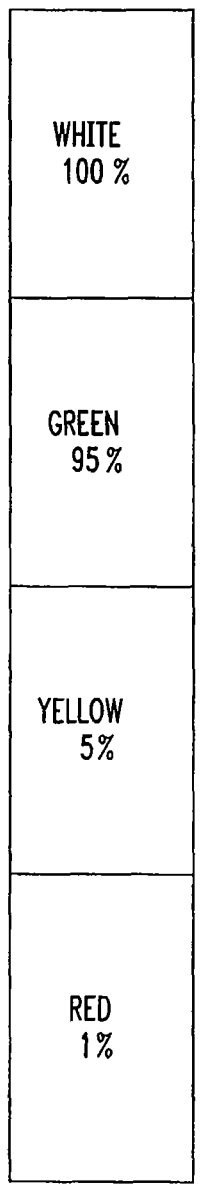
FIG. 3A-FIG. 3C show color coding schemes for retinal thickness display bands.

The plots are displayed as color graphical images. Herein, color graphical images include images displayed on a video monitor and images printed on a printout. Herein, color graphical images include monochrome images (such as black and white images). In FIG. 1A-FIG. 1C, colors are indicated by W=White, G=Green, Y=Yellow, and R=Red. The conventional color scheme is illustrated in FIG. 3A. At each measurement locus, thickness measurements for a normal (healthy) population of retinas have been accumulated (the data may be grouped according to parameters such as the age of the patient). Thickness measurements vary from patient to patient, and the statistical distribution of thicknesses is referred to as the normative distribution. The color codes refer to the following statistical ranges—Red: 1% of the normal population fall within the red band; Yellow: 4% fall within the yellow band, 5% fall within or below the yellow band; Green: 90% fall within the green band, 95% fall within or below the green band, and White: 5% fall within the white band, 100% fall within or below the white band. In statistical terms, if $T^p$ is the p-th percentile value of thickness T, then $T^1$, $T^5$, $T^{95}$, and $T^{100}$ correspond to $T^r$, $T^y$, $T^g$, and $T^w$, where $T^r$, $T^y$, $T^g$, and $T^w$ are the tops of the red, yellow, green, and white bands, respectively.

Figure 2:
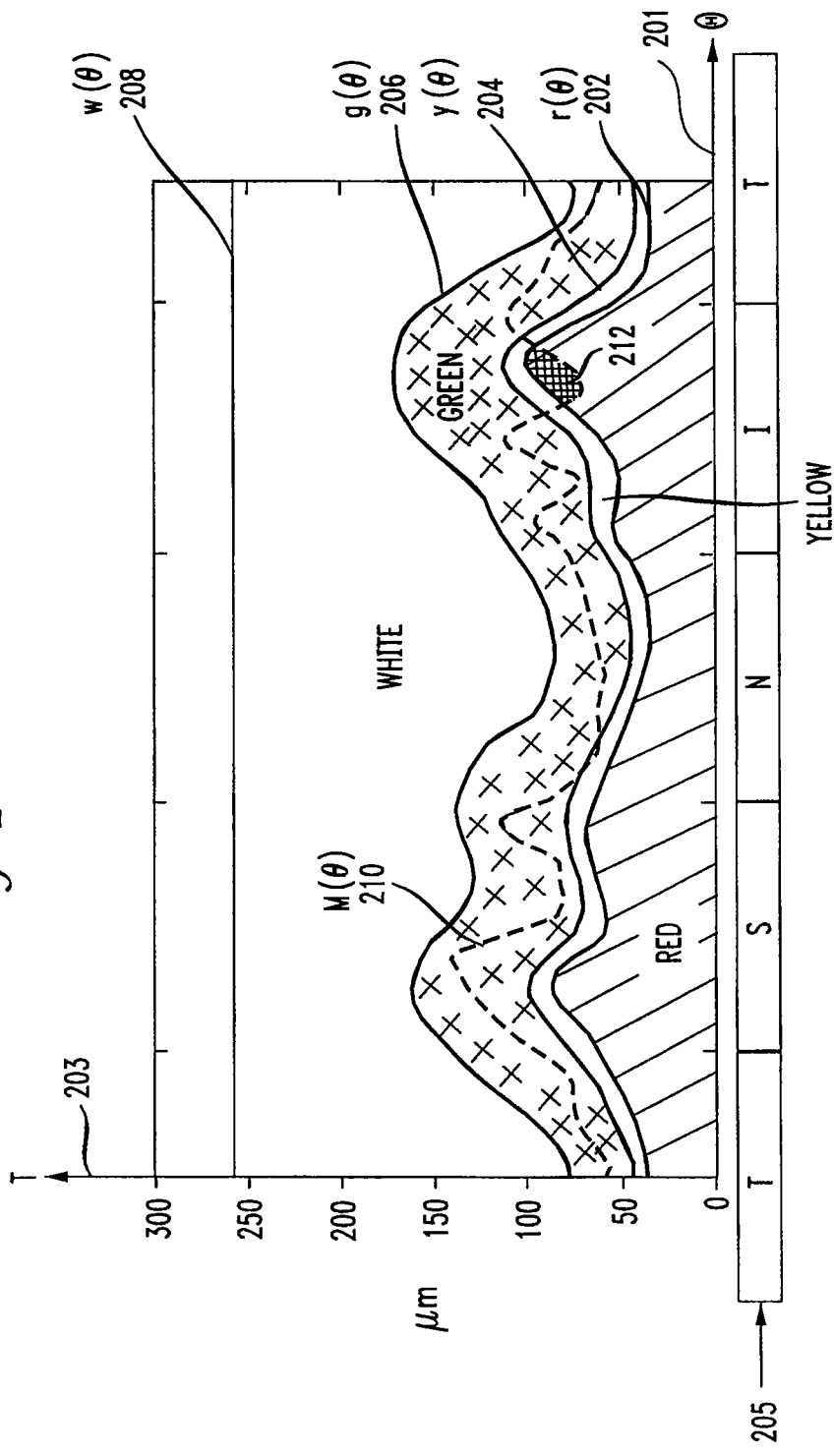
FIG. 2 shows a retinal thickness profile as a function of polar angle.
Figure 5A:
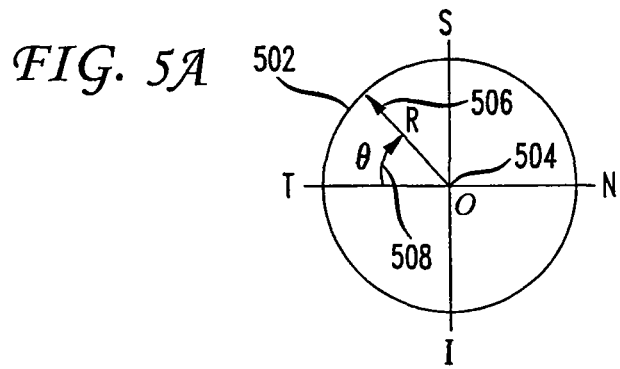
FIG. 5A-FIG. 5C show a graphical analysis of retinal thickness.

The color ranges are also illustrated in FIG. 2, which shows plots of thickness T 203 as a function of θ 201 on a TSNIT diagram. The reference geometry is shown in FIG. 5A. The center of the circle 502 is O 504, and the radius is R 506. The polar angle θ 508 is measured clockwise from the O-T axis. In FIG. 2, the red band corresponds to the area below the function $T^1$=r(θ) (represented by the plot 202). The yellow band falls in the area below the function $T^5$=y(θ) (represented by the plot 204) and above r(θ). The green band falls in the area below $T^{95}$=g(θ) (represented by plot 206) and above y(θ). The white band falls in the area below $T^{100}$=w(θ) (represented by plot 208) and above g(θ). To simplify the figure and to allow for anomalous values, w(θ) is shown as a large constant value. The function M(θ) (represented by plot 210) corresponds to a set of measured values. Note that, in region 212, M(θ) is less than r(θ). Region 212 is an abnormal region. Abnormal regions are discussed in further detail below.

FIG. 1A-FIG. 1C show limitations of the conventional data presentation. For example, consider the measurement loci on the 90-deg arc 142 between the S and N reference points. [Note that the dashed line representing arc 142 is shown spaced apart from the circle only to highlight the arc in the figures. The measurement loci fall along the circle.] In FIG. 1A, arc 142 includes a portion of arc 112 (average thickness=$<T_{1,2}>$, color code=green) and a portion of arc 113 (average thickness=$<T_{1,3}>$, color code=green). In FIG. 1B, arc 142 includes a portion of arc 122 (average thickness=$<T_{2,2}>$, color code=green) and the complete arc 123 (average thickness=$<T_{2,3}>$, color code=yellow). In FIG. 1C, arc 142 includes a portion of arc 133 (average thickness=$<T_{3,3}>$, color code=green), the complete arc 134 (average thickness=$<T_{3,4}>$, color code=red), and a portion of arc 135 (average thickness=$<T_{3,5}>$, color code=yellow). Note that the color bands change abruptly, and local variations in thickness are difficult to identify and track.

Figure 3B:
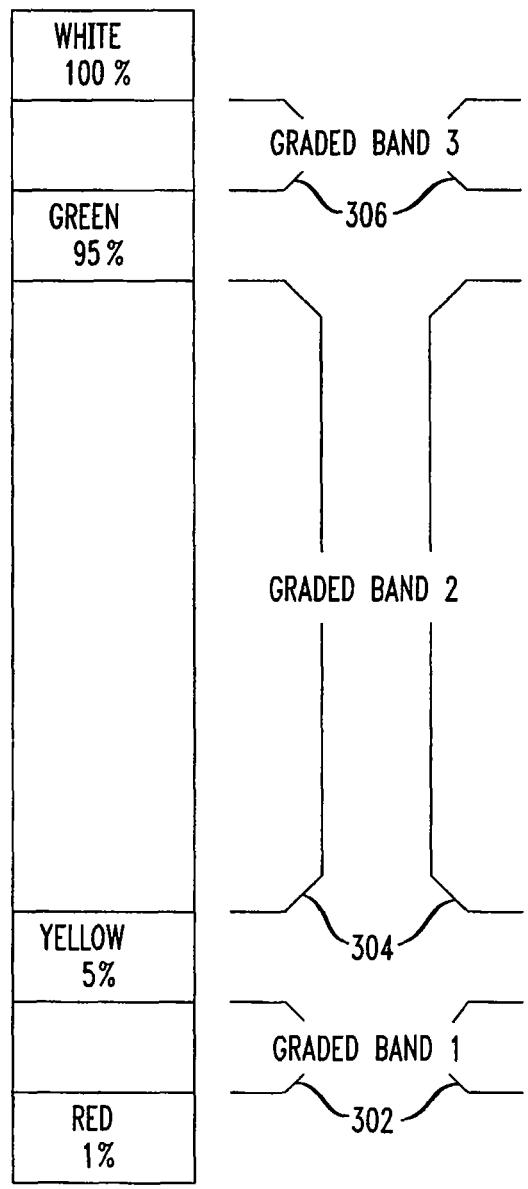
Figure 3C:
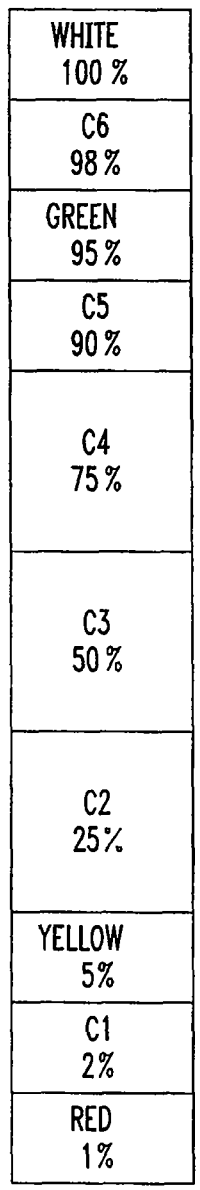

In FIG. 3B and FIG. 3C, the color code is expanded to show higher resolution in the thickness range and higher resolution in the variation in thickness range from one arc to another. In FIG. 3B, graded band 1 302 is introduced between the red band and the yellow band. Graded band 2 304 is introduced between the yellow band and the green band. Graded band 3 306 is introduced between the green band and the white band. Examples of graded bands are given in FIG. 3C. Here, graded band 1 302 comprises one additional color band with color C1; 2% of the normal population fall within or below the C1 band ($T^2$=$T^{C1}$). Graded band 2 304 comprises four additional color bands (with colors C2-C5): 25% fall within or below the C2 band ($T^{25}$=$T^{C2}$), 50% fall within or below the C3 band ($T^{50}$=$T^{C3}$), 75% fall within or below the C4 band ($T^{75}$=$T^{C4}$), and 90% fall within or below the C5 band ($T^{90}$=$T^{C5}$) Graded band 3 306 comprises one additional color band with color C6; 98% of the normal population fall within or below the C6 band ($T^{98}$=$T^{C6}$).

Herein, a range of a retinal parameter is mapped to a display band (discussed below). A retinal parameter is any parameter that characterizes a property of the retina. Examples of retinal parameters include retinal thickness, density, diameters of anatomical features, and the number of anatomical features per unit area. Herein, retinal thickness may refer to either total thickness or thickness of individual layers, depending on the application, as specified by a user. In an embodiment of the invention, retinal parameters are calculated from a 3-D volume dataset, such as a 3-D volume dataset acquired from 3D-OCT measurements. Retinal parameters may also be measured by other ophthalmological techniques, such as confocal scanning laser ophthalmoscopy and scanning laser polarimetry. A statistical distribution of a retinal parameter is acquired from a user-defined reference population of retinas. The reference population, for example, may be a normative population of retinas in healthy eyes. The reference population may also be a population of retinas in eyes afflicted with glaucoma, diabetic retinopathy, or other abnormal condition. The statistical distribution is a function of the measurement loci.

Herein, a range of a retinal parameter is bounded by a lower limit and an upper limit of the retinal parameter. A statistical range of the reference population has values of the retinal parameter falling within the range. The lower limit and the upper limit may correspond to user-defined percentiles (or equivalent quantiles). Herein, a display band refers to a visually distinct graphical element. A display band may be characterized, for example, by color, intensity, shading, and cross-hatching. Herein, a specific range of retinal parameters is mapped to a specific display band. For example, in FIG. 2, the yellow display band (as a function of θ for a fixed value of the radius) has a lower limit of $T^1=T^r=r(\theta)$ and an upper limit of $T^5=T^y=y(\theta)$. Ranges of retinal parameters may be mapped to a quasi-continuous series of display bands. For example, in FIG. 3B, graded band 2 may comprise a user-defined number of display bands.

Figure 5B:
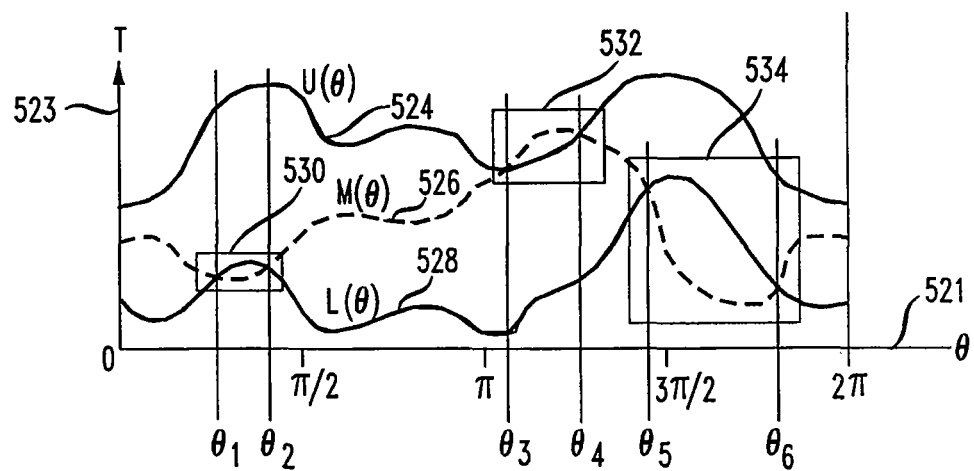

In an embodiment of the invention, variations in retinal thickness are characterized as a ratio of areas in a T 523 vs. θ 521 plot, as shown in FIG. 5B. The function $T_U=U(\theta)$ 524 represents an upper reference limit of thickness; similarly, the function $T_L=L(\theta)$ 528 represents a lower reference limit of thickness. $U(\theta)$ and $L(\theta)$ are user-defined functions. In one example, the lower limit is the 1-st percentile, $L(\theta)=T^1(\theta)$; and the upper limit is the 95-th percentile, $U(\theta)=T^{95}(\theta)$. In another example, the lower limit is the 5-th percentile, $L(\theta)=T^5(\theta)$; and the upper limit is the 90-th percentile, $U(\theta)=T^{90}(\theta)$.

The function $T_M=M(\theta)$ 526 represents the set of measured values of thickness. Herein, a measured value $M(\theta)$ is considered to be normal if it falls between the lower and upper reference limits, $L(\theta) \leq M(\theta) \leq U(\theta)$. A measured value $M(\theta)$ is considered to be abnormally low (thin) if it falls below the lower reference limit, $M(\theta)<L(\theta)$. Similarly, a measured value $M(\theta)$ is considered to be abnormally high (thick) if it falls above the upper reference limit, $M(\theta)>U(\theta)$. Eye diseases such as glaucoma and diabetic retinopathy are associated with loss of retinal tissue; therefore, abnormally low measurements are of specific interest. Abnormally high measurements, however, may also be characterized by the techniques described herein, if needed.

In FIG. 5B, the regions highlighted by box 530, box 532, and box 534 are regions of abnormal measurements. Referring to box 530, the retina is abnormally thin for $\theta_1<\theta<\theta_2$. Referring to box 532, the retina is abnormally thick for $\theta_3<\theta<\theta_4$. Referring to box 534, the retina is abnormally thin for $\theta_5<\theta<\theta_6$. An abnormal region may be specified by minimum and maximum angles, $\theta_{min}<\theta<\theta_{max}$; or equivalently by the central angle $\theta_c=(\theta_{min}+\theta_{max})/2$ and the included angle $\Delta\theta_c=(\theta_{max}-\theta_{min})$ [that is, $\theta_{min}=(\theta_c-\Delta\theta_c/2)$ and $\theta_{max}=(\theta_c+\Delta\theta_c/2)$].

In an embodiment of the invention, the degree of abnormality (D) is characterized by a ratio of areas:

$$D(\theta_1 < \theta < \theta_2) = \frac{\int_{\theta_1}^{\theta_2} M(\theta)d\theta}{\int_{\theta_1}^{\theta_2} L(\theta)d\theta} \quad (E1)$$

$$D(\theta_3 < \theta < \theta_4) = \frac{\int_{\theta_3}^{\theta_4} M(\theta)d\theta}{\int_{\theta_3}^{\theta_4} U(\theta)d\theta} \quad (E2)$$

$$D(\theta_5 < \theta < \theta_6) = \frac{\int_{\theta_5}^{\theta_6} M(\theta)d\theta}{\int_{\theta_5}^{\theta_6} L(\theta)d\theta} \quad (E3)$$

Note: If $L(\theta)$, $U(\theta)$, and $M(\theta)$ are represented by discrete sets of values, then the integrals may be replaced by the corresponding summations. For abnormally thin regions, D<1; for abnormally thick regions, D>1. Note that abnormalities may be characterized by other functions of the integrals. For example, the difference of areas may be used instead of the ratio of areas.

A user, such as an eye doctor, may use the value of D to help diagnose the health of the eye. For example, as discussed above, in glaucoma, retinal tissue is lost, and the retina is abnormally thin. The eye doctor may define a threshold value $D_0$ such that, if $D<D_0$, additional user-defined ophthalmological diagnostics are ordered. The threshold value $D_0$ may be specified according to user-defined criteria. For example, it may be based on historic data acquired from a population of glaucoma patients.

Figure 5C:
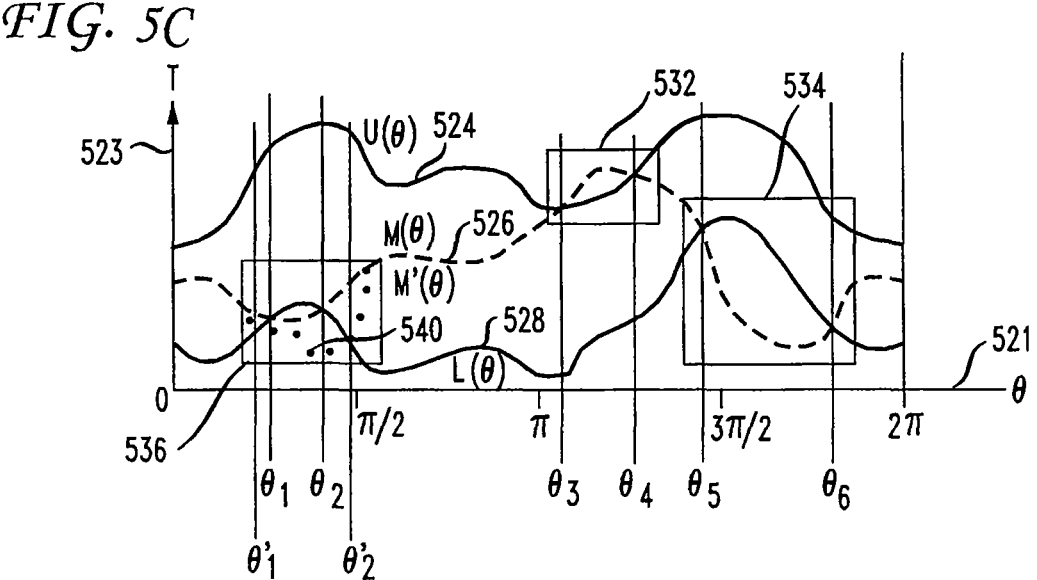

FIG. 5C represents a set of measurements $M'(\theta)$ 540 taken of the same retina at a later time. Here, $M'(\theta)$ closely tracks $M(\theta)$ except in the region highlighted by box 536. Note that there has been additional thinning of the retina, and the abnormal region has spread from $\theta_1<\theta<\theta_2$ to $\theta'_1<\theta<\theta'_2$, where $\theta'_1<\theta_1$ and $\theta'_2>\theta_2$. The new ratio D' is then:

$$D'(\theta'_1 < \theta < \theta'_2) = \frac{\int_{\theta'_1}^{\theta'_2} M'(\theta)d\theta}{\int_{\theta'_1}^{\theta'_2} L(\theta)d\theta} \quad (E4)$$

The additional degradation of the retina in this region may be characterized by a function of D and D', such as the difference D'−D, or the ratio D'/D. An eye doctor may diagnose the health of the eye partly by monitoring the angular interval (minimum angle, maximum angle) and D values (or other characterization values) as a function of time.

Figure 6A:
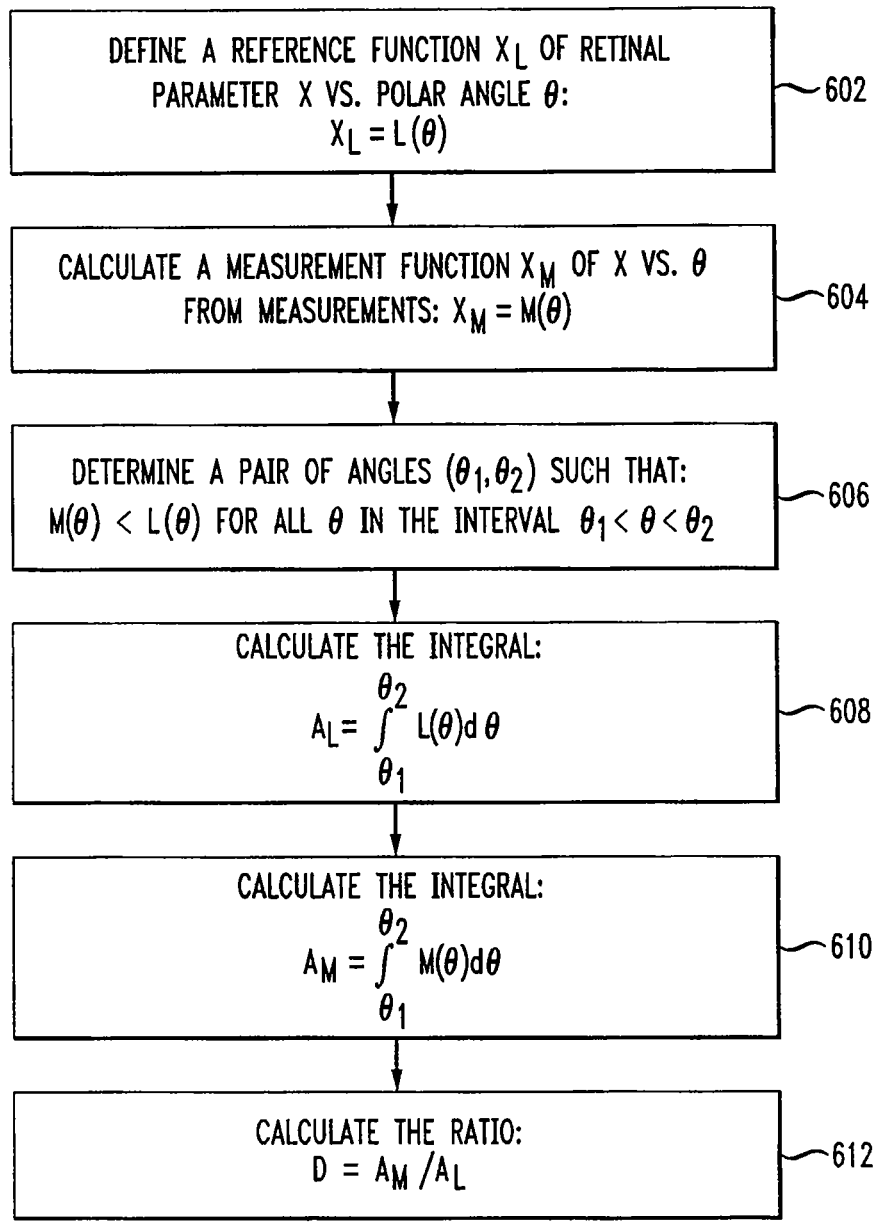
FIG. 6A shows a flowchart of steps for characterizing an abnormal retinal region.

A process for characterizing a retinal parameter X, according to an embodiment of the invention, is summarized in the flowchart of steps shown in FIG. 6A. In step 602, a reference function $X_L$ of thickness X vs. polar angle θ at a fixed radius Ro is defined by a user. For example, $X_L$ may represent the p-th percentile value of X calculated from a reference population. The process then passes to step 604, in which a function $X_M=M(\theta)$ (herein called the measurement function) is calculated from measured values of X. The measurements may be acquired by 3-D OCT or other ophthalmological techniques. The process then passes to step 606 in which a pair of angles $(\theta_1, \theta_2)$ is identified such that $M(\theta)<L(\theta)$ for all θ in the interval $\theta_1<\theta<\theta_2$. This interval (corresponding to an arc with radius $R_0$) designates an abnormally thin region. There may be multiple such intervals. The process then passes to step 608 in which the integral $$A_L = \int_{\theta_1}^{\theta_2} L(\theta)d\theta$$

under the reference function $X_L=L(\theta)$ is calculated. The process then passes to step 610 in which the integral $$A_M = \int_{\theta_1}^{\theta_2} M(\theta)d\theta$$

under the measurement function $X_M=M(\theta)$ is calculated. The process then passes to step 612 in which the ratio $D=A_M/A_L$ is calculated. The position and size of the abnormally thin region is characterized by $(\theta_1, \theta_2)$ and the degree of abnormality (deviation of measured thickness distribution from reference thickness distribution) is D.

Figure 4:
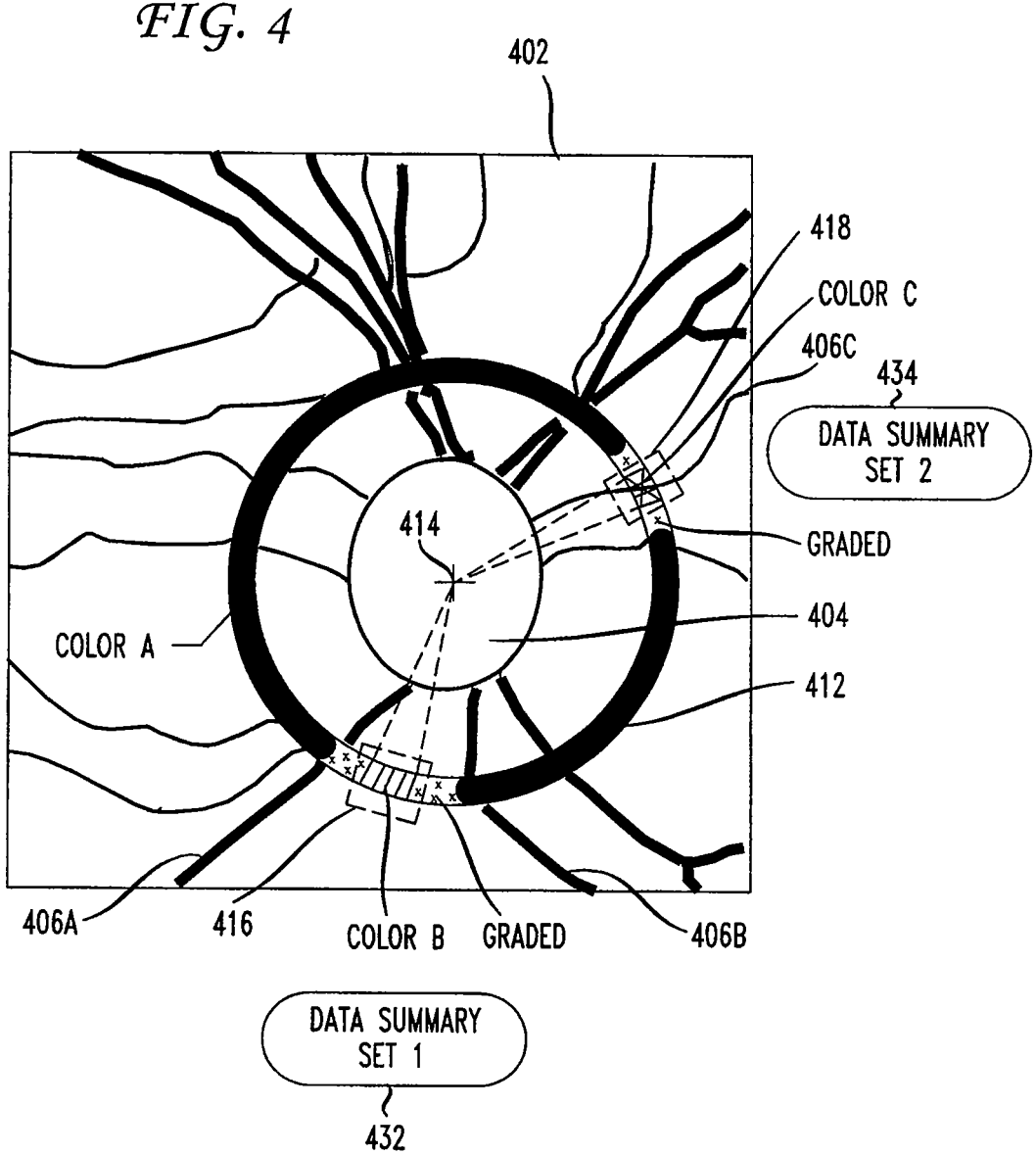
FIG. 4 shows a combined circular profile map and fundus image.

FIG. 4 shows a circular profile map 412, such as a circular profile map of retinal thickness, superimposed on a two-dimensional (2-D) image 402 of the retina. As discussed above, other retinal parameters may be mapped. Note that a function of a retinal parameter is also a retinal parameter. For example, the degree of abnormality (D) is a retinal parameter. Examples of 2-D image 402 are a color fundus image, a black-and-white fundus image, a 2-D composite image rendered from a 3-D OCT volume dataset, and a combination of a fundus image and a 2-D composite image. U.S. patent application Ser. No. 11/800,186, which is incorporated by reference herein, describes a technique for rendering a 2-D composite image from a 3-D OCT volume dataset and registering the dataset with a fundus image. Retinal thickness (and other retinal parameters) may be calculated from the 3-D OCT volume dataset and mapped to a 2-D image. In FIG. 4, anatomical features such as optic disc 404 and blood vessels 406A-406C are visible. The center 414 of circular profile map 412 is positioned at the center of optic disc 404. In other embodiments of the invention, the center 414 of circular profile map 412 may be positioned at other points on the retina, as described in U.S. patent application Ser. No. 12/262,620, which is incorporated by reference herein.

As discussed previously, retinal thickness may be measured by other diagnostic instruments, such as the Zeiss Stratus OCT 3. Circular profile map 412 may be generated from a circle scan and superimposed on 2-D image 402. Circular profile map 412 may be registered with 2-D image 402 by superimposing the center of the circle scan onto the center of the optic disc 404.

In FIG. 4, circular profile map 412 is not divided into arbitrary sectors. To aid in diagnosis, only specific regions of interest (region 416 and region 418) are highlighted by differentiating display bands. Regions of interest are defined according to user-specified criteria. For example, the circular profile map 412 may represent thickness values, and the colors (Color A, Color B, and Color C) may represent percentile ranges, as shown in FIG. 3A-FIG. 3C. Note the graded display bands between Color A and Color B in region 416 and the graded display bands between Color A and Color C in region 418. In another example, the circular profile map may represent D values. Normal regions (D=1), for example, are mapped to Color A; abnormally thin regions (D<1) are mapped to Color B; and abnormally thick regions (D>1) are mapped to Color C. Further differentiation may be achieved by mapping specific ranges of D to specific display bands.

In FIG. 4, regions including blood vessels (and other anatomical features) are readily discernible. For example, blood vessels 406A and 406 B run near the outer boundaries of region 416, and blood vessel 406C runs through region 418. A user may analyze potential correlation of thickness values (or other retinal parameters) with the presence of blood vessels (or other anatomical features).

In FIG. 4, a data summary set for an abnormal region is displayed near the abnormal region. For example, data summary set 1 432 is associated with region 416, and data summary set 2 434 is associated with region 418. The elements of a data summary set characterize properties of the associated region. The elements are user defined. Examples of elements include $\theta_{min}$ and $\theta_{max}$ (or equivalent $\theta_c$ and $\Delta\theta_c$); average and median values of thickness T; and D value. A data summary set may also be associated with a normal region, if desired.

Figure 7A:
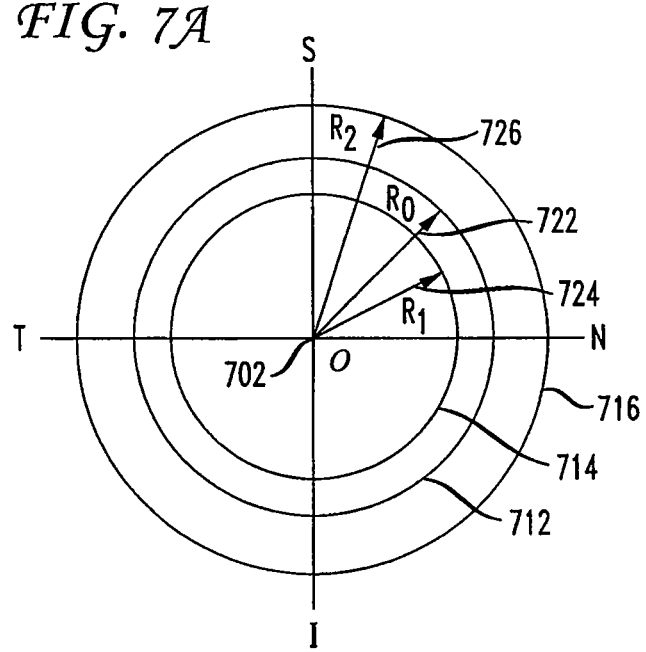
FIG. 7A shows circular profile maps with different radii.

In a conventional circle scan, the measurement loci all fall along a circle with a fixed radius of 1.73 mm. As shown in FIG. 7A, measurements may be taken along circles with different radii to characterize extended regions of the retina. The origin is located at O 702. Circle 712 has radius $R_0$ 722; circle 714 has radius $R_1$ 724; and circle 716 has radius $R_2$ 726. A method for correlating normative data previously measured from circle scans at a single fixed radius with data measured from circle scans at different radii is described in U.S. Patent Application Publication No. 2009/0033868, which is incorporated by reference herein.

Figure 7B:
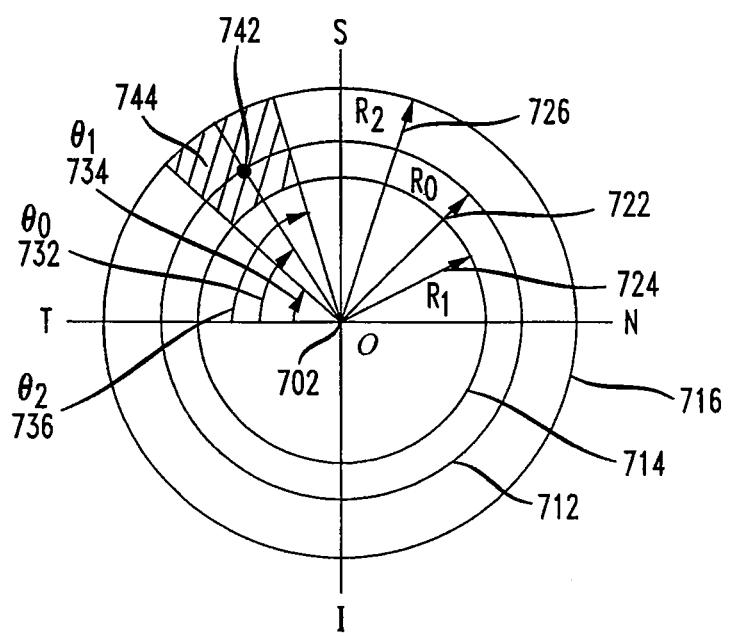
FIG. 7B shows measurements of retinal thickness in a neighborhood around a measurement locus.

As shown in FIG. 7B, measurements may be sampled over neighborhoods on the retina instead of at loci along a circle. Sampling measurements in a neighborhood around a measurement locus reduces errors due to eye movement and errors in determining the position of the measurement locus. In FIG. 7B, the origin is located at O 702. For a circle scan, measurement loci are located along circle 712 with radius $R_0$ 722. A specific locus, designated $P_0$ 742, has the polar coordinates $(R_0, \theta_0)$. The angle $\theta_0$ is referenced in FIG. 7B as $\theta_0$ 732. Measurement loci are located in the annular region between circle 714 with radius $R_1$ 724 and circle 716 with radius $R_2$ 726. The neighborhood $\sigma_0$ 744 about locus $P_0$ 742 is defined by $(R_1 \leq R \leq R_2, \theta_1 \leq \theta \leq \theta_2)$. The angle $\theta_1$ is referenced as $\theta_1$ 734; the angle $\theta_2$ is referenced as $\theta_2$ 736. A statistical summary value, such as the average or median, may be calculated for values of the retinal thickness (or other retinal parameter) within $\sigma_0$ 744. Similar neighborhoods are defined for other measurement loci. The set of summary values acquired from all neighborhoods may then be mapped to a circular profile map superimposed on a fundus image, or other 2-D image. One skilled in the art may develop embodiments for other neighborhood topologies (for example, a neighborhood may be a circular region around a measurement locus).

Figure 6B:
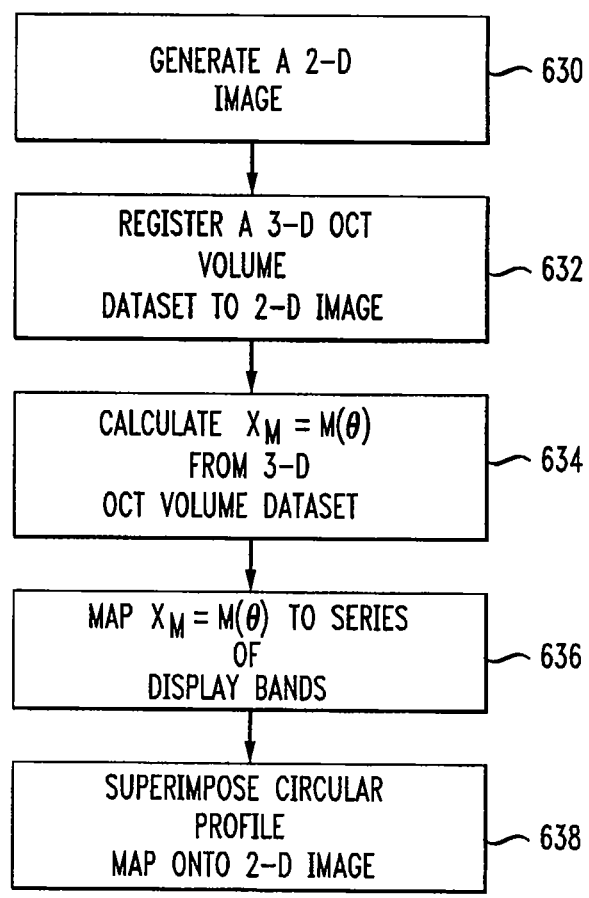
FIG. 6B shows a flowchart of steps for combining a circular profile map with a fundus image.

A method for simultaneously displaying a 2-D image and a circular profile map is summarized in the flowchart of steps shown in FIG. 6B. In step 630, a 2-D image is generated on a display, such as a computer monitor. The 2-D image may be a fundus image, a 2-D composite image generated from a 3-D OCT volume dataset, a combination of a fundus image and a 2-D composite image, or any other 2-D ophthalmological image. The process then passes to step 632, in which a 3-D OCT volume dataset (or other 3-D volume dataset) is registered to the 2-D image. The process then passes to step 636, in which a measurement function $X_M = M(\theta)$ is calculated from the 3-D OCT volume dataset. The process then passes to step 636, in which the measurement function $X_M = M(\theta)$ is mapped to a quasi-continuous series of display bands to generate a circular profile map. The process then passes to step 638, in which the circular profile map is superimposed onto the 2-D fundus image. The position and orientation of the circular profile map is properly placed with respect to the 2-D image via the previous registration process in step 632. As discussed above, in addition to measurements calculated from a 3-D OCT volume dataset, measurements may be taken by other ophthalmological techniques and superimposed on a 2-D image (with appropriate registration schemes).

Figure 9C:
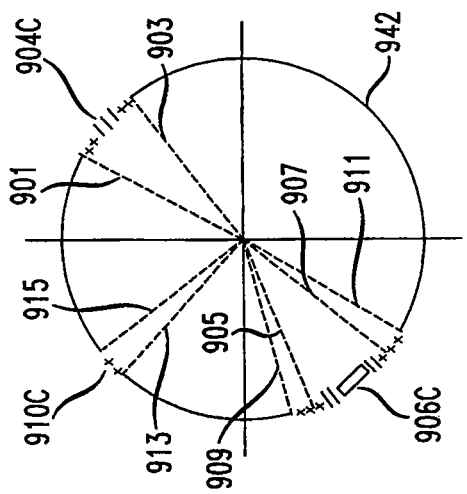
FIG. 9A-FIG. 9D show progression of retinal abnormalities as a function of time.
Figure 9B:
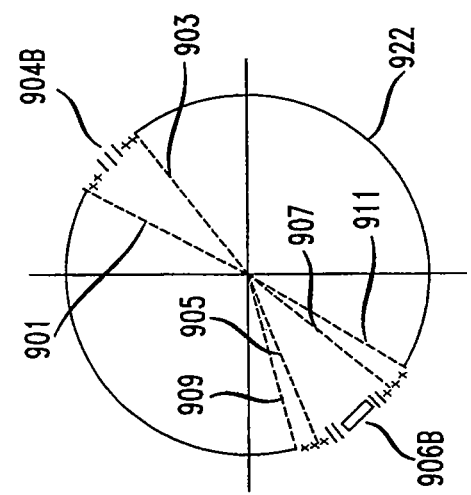
Figure 9A:
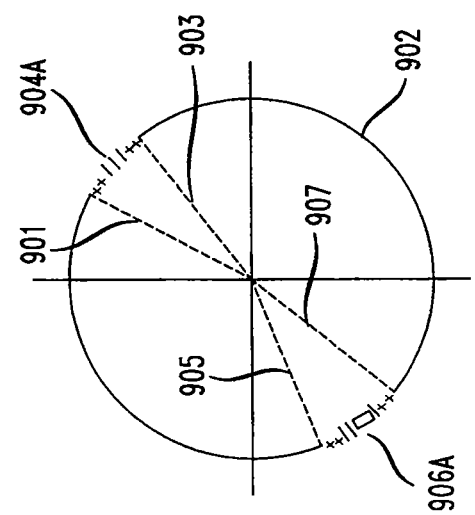

Progression of abnormalities over time may be displayed as a set of concentric circular profile maps, as shown in FIG. 9A-FIG. 9D. To simplify the figures, the 2-D images are not shown. In FIG. 9A, circular profile map 902 displays data taken at an initial time $t_0$. Two abnormal regions, the first represented by arc 904A and the second represented by arc 906A, are apparent. Arc 904A is bounded by radial line 901 ($\theta = \theta_1$) and radial line 903 ($\theta = \theta_2$). Note: The angles follow the convention shown in FIG. 5A and are not shown in FIG. 9A-FIG. 9D. Arc 906A is bounded by radial line 905 ($\theta = \theta_3$) and radial line 907 ($\theta = \theta_4$). In FIG. 9B, circular profile map 922 displays data taken at a time $t_1$, where $t_1 > t_0$. There are still two abnormal regions. Relative to the circular profile map 902, the first abnormal region, represented by arc 904B, remains stable, but the second abnormal region, represented by arc 906B, has grown. Arc 906B is bounded by radial line 909 ($\theta = \theta_5$) and radial line 911 ($\theta = \theta_6$). Similarly, in FIG. 9C, circular profile map 942 displays data taken at a time $t_2$, where $t_2 > t_1$. Relative to circular profile map 922, the first abnormal region, represented by arc 904C, and the second abnormal region, represented by arc 908C, remain unchanged. A third abnormal region, represented by arc 910C, however, has emerged. Arc 910C is bounded by radial line 913 ($\theta = \theta_7$) and radial line 915 ($\theta = \theta_8$).

Figure 9D:
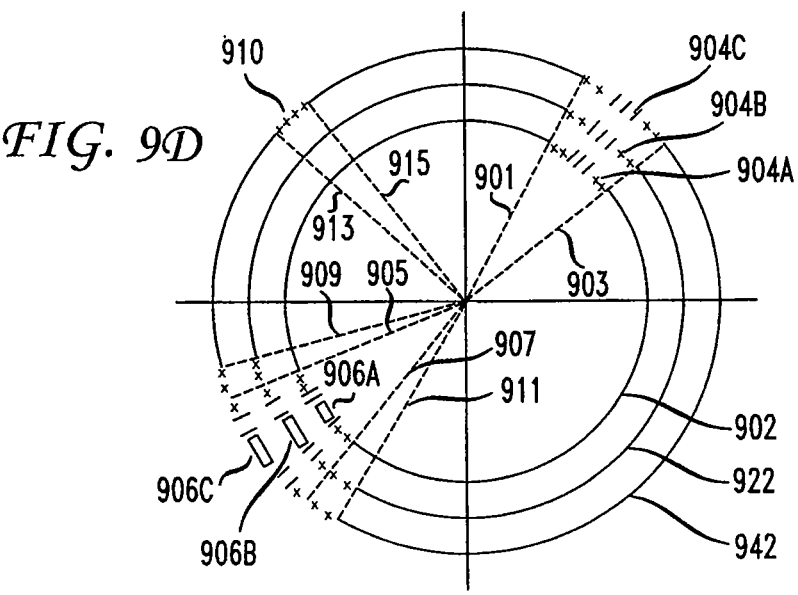

FIG. 9A-FIG. 9C are displayed side-by-side and progression of abnormal regions is difficult to visualize. In FIG. 9D, circular profile map 902, circular profile map 922, and circular profile map 942 are merged into a set of concentric circular profile maps. Note that in FIG. 9A-FIG. 9C the circular profile maps all have the same radius. If the circular profile maps are simply superimposed on top of each other, details are difficult to resolve. In FIG. 9D, the radii of the circular profile maps are offset to provide a visual sequence. Circular profile map 902, circular profile map 922, and circular profile map 942 are plotted in order of increasing radius. In this instance, the radius does not necessarily correspond to the radius of measurement loci. The regions of interest are then delimited by radial lines with specific values of $\theta$. For example, the abnormal region represented by arc 904A, arc 904B, and arc 904C stays bounded by radial line 901 ($\theta = \theta_1$) and radial line 903 ($\theta = \theta_2$). It is therefore stable over time. The display bands are scaled appropriately to account for the different radii. Similarly, the abnormal region initially represented by arc 906A increases to the abnormal region represented by arc 906B. It is then stable, as represented by arc 906C.

Figure 8:
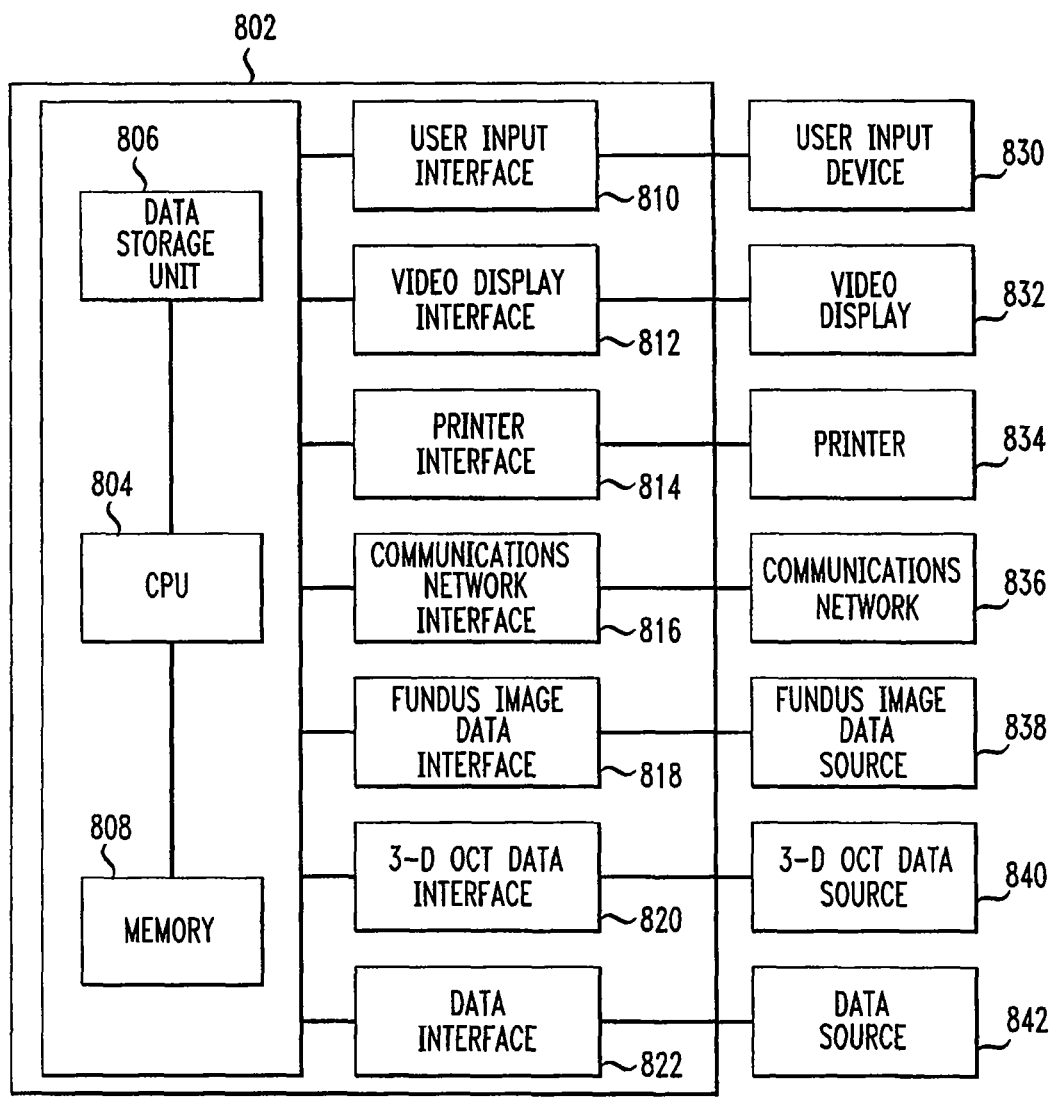
FIG. 8 shows a schematic of a measurement, analysis, and image processing system implemented with a computer.

One embodiment of a measurement, data processing, image processing, and data display system for circular profile analysis of retinal characteristics may be implemented using a computer. As shown in FIG. 8, computer 802 may be any type of well-known computer comprising a central processing unit (CPU) 804, memory 808, and data storage unit 806. Data storage unit 806 may comprise a hard drive, non-volatile memory, or other computer readable media (such as a compact disc or digital video disc).

Computer 802 may further comprise a user input interface 810, which provides communication between computer 802 and a user input device 830, such as a keyboard or mouse. Computer 802 may further comprise a video display interface 812, which transforms signals from CPU 804 to signals which drive a video display 832, such as a computer monitor. Video display 832 may be used to display a combined fundus image and circular profile map, such as the one shown in FIG. 4. Computer 802 may further comprise a printer interface 814, which provides communication between computer 802 and a printer 834. Printer 834 may be used to print a combined fundus image and circular profile map, such as the one shown in FIG. 4. Computer 802 may further comprise a communications network interface 816, which comprises a connection to a communications network 836. Communications network 836 may be used to transport data, computer program instructions, user commands, and video signals.

Computer 802 may further comprise a fundus image data interface 818, which provides communication between computer 802 and a fundus image data source 838, such as a digital fundus camera. Computer 802 may further comprise a 3-D OCT data interface 820, which provides communication between computer 802 and a 3-D OCT data source 840, such as a 3-D OCT ophthalmic diagnostic instrument. Computer 802 may further comprise other data interfaces, such as data interface 822, which provides communication between computer 802 and other data sources, such as data source 842. Data source 842, for example, may be an instrument which performs conventional circle scans, such as a Zeiss OCT Stratus 3. Fundus image data source 838, 3-D OCT data source 840, and data source 842 may also be databases containing data which is transferred to data storage unit 806 via fundus image data interface 818, via 3-D OCT data interface 820, and via data interface 822, respectively. User input device 830, video display 832, printer 834, fundus image data source 838, 3-D OCT data source 840, and data source 842 may also remotely connect to computer 802 via communications network 836 and communications network interface 816. Computers are well known in the art and will not be described in detail herein. One skilled in the art will recognize that an implementation of an actual computer may contain other components as well, and that FIG. 8 is a high-level representation of some of the components of a computer for illustrative purposes.

As is well known, a computer operates under control of computer software which defines the overall operation of the computer and applications. CPU 802 controls the overall operation of the computer and applications by executing computer program instructions which define the overall operation and applications. The computer program instructions may be stored in data storage unit 806 and loaded into memory 808 when execution of the program instructions is desired. The method steps shown in FIG. 6A and FIG. 6B, for example, may be defined by computer program instructions stored in the memory 808 or in the data storage unit 806 (or in a combination of memory 808 and data storage unit 806) and controlled by the CPU 804 executing the computer program instructions. For example, the computer program instructions may be implemented as computer executable code programmed by one skilled in the art to perform algorithms implementing the method steps shown in FIG. 6A and FIG. 6B. Accordingly, by executing the computer program instructions, the CPU 802 executes algorithms implementing the method steps shown in FIG. 6A and FIG. 6B.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for characterizing a retinal parameter as a function of a polar angle $\theta$, the method comprising the steps of:

determining an interval of polar angles bounded by a first polar angle and a second polar angle wherein, at each polar angle within the interval, the value of a measurement parameter function is greater than the value of a reference parameter function;

calculating a first integral comprising an integral of the reference parameter function over the interval;

calculating a second integral comprising an integral of the measurement parameter function over the interval; and calculating a characterization value based at least in part on the first integral and the second integral.

2. The method of claim 1, wherein the step of calculating a first characterization value comprises the step of:

calculating a first ratio comprising the ratio of the second integral to the first integral.

3. The method of claim 2, further comprising the step of:
diagnosing the health of an eye based at least in part on the first ratio.

4. The method of claim 2, further comprising the steps of:
comparing the first ratio to a threshold value; and
performing user-defined ophthalmological diagnostics if the first ratio is greater than the threshold.

5. The method of claim 1, wherein:
the step of calculating a first integral comprises the step of calculating:

$$A_L = \int_{\theta_1}^{\theta_2} L(\theta) d\theta,$$

wherein $\theta_1$ is the first polar angle, $\theta_2$ is the second polar angle, and $L(\theta)$ is the reference parameter function; and
the step of calculating a second integral comprises the step of calculating:

$$A_M = \int_{\theta_1}^{\theta_2} M(\theta) d\theta,$$

wherein $M(\theta b)$ is the first measurement parameter function.

6. The method of claim 5, further comprising the step of:
calculating a first ratio $D = A_M/A_L$.

7. The method of claim 1, wherein the retinal parameter comprises a retinal thickness.

8. The method of claim 1, wherein the first measurement parameter function is generated from a three-dimensional optical coherence tomography volume dataset.

9. The method of claim 1, wherein the reference parameter function represents a p-th percentile value of a reference population.

10. The method of claim 1, wherein the first measurement parameter function is generated from values of the retinal parameter at each measurement locus in a set of measurement loci along a circle.

11. The method of claim 1, wherein the first measurement parameter function is generated from values of the retinal parameter in a neighborhood about each measurement locus in a set of measurement loci along a circle.

12. The method of claim 1, wherein the first measurement parameter function is based at least in part on values of the retinal parameter at a first time.

13. The method of claim 12, further comprising the steps of:
receiving a second measurement parameter function based at least in part on values of the retinal parameter at a second time;
determining a second interval of polar angles bounded by a third polar angle and a fourth polar angle wherein, at each polar angle within the second interval, the value of the second measurement parameter function is greater than the value of the reference parameter function;
calculating a third integral comprising an integral of the reference parameter function over the second interval;
calculating a fourth integral comprising an integral of the second measurement parameter function over the second interval; and
calculating a second characterization value based at least in part on the third integral and the fourth integral.

14. The method of claim 13, wherein the step of calculating a second characterization value comprises the step of:
calculating a second ratio comprising the ratio of the fourth integral to the third integral.

15. The method of claim 13, further comprising the step of:
diagnosing the health of an eye based at least in part on at least one of:
the first polar angle;
the second polar angle;
the third polar angle;
the fourth polar angle;
the first characterization value; and
the second characterization value.

16. An apparatus for characterizing a retinal parameter as a function of a polar angle θ, the apparatus comprising:
means for determining an interval of polar angles bounded by a first polar angle and a second polar angle wherein, at each polar angle within the interval, the value of a measurement parameter function is greater than the value of a reference parameter function;
means for calculating a first integral comprising an integral of the reference parameter function over the interval;
means for calculating a second integral comprising an integral of the
measurement parameter function over the interval; and
means for calculating a characterization value based at least in part on the first integral and the second integral.

17. The apparatus of claim 16, wherein the means for calculating a first characterization value comprises:
means for calculating a first ratio comprising the ratio of the second integral to the first integral.

18. The apparatus of claim 16, wherein:
the means for calculating a first integral comprises means for calculating:

$$A_L = \int_{\theta_1}^{\theta_2} L(\theta) d\theta,$$

wherein $\theta$hd 1 is the first polar angle, $\theta_2$ is the second polar angle, and $L(\theta)$ is the reference parameter function; and
the means for calculating a second integral comprises means for calculating:

$$A_M = \int_{\theta_1}^{\theta_2} M(\theta) d\theta,$$

wherein $M(\theta)$ is the first measurement parameter function.

19. The apparatus of claim 18, wherein the means for calculating a first characterization value based at least in part on the first integral and the second integral comprises:
means for calculating a first ratio $D = A_m/A_L$.

20. The apparatus of claim 16, further comprising:
means for generating the first measurement parameter function from values of the retinal parameter at each measurement locus in a set of measurement loci along a circle.

21. The apparatus of claim 16, further comprising:
means for generating the first measurement parameter function from values of the retinal parameter in a neighborhood about each measurement locus in a set of measurement loci along a circle.

22. The apparatus of claim 16, wherein the first measurement parameter function is based at least in part on values of the retinal parameter at a first time.

23. The apparatus of claim 22, further comprising:
means for receiving a second measurement parameter function based at least in part on values of the retinal parameter at a second time;
means for determining a second interval of polar angles bounded by a third polar angle and a fourth polar angle wherein, at each polar angle within the second interval, the value of the second measurement parameter function is greater than the value of the reference parameter function;
means for calculating a third integral comprising an integral of the reference parameter function over the second interval;
means for calculating a fourth integral comprising an integral of the second measurement parameter function over the second interval; and
means for calculating a second characterization value based at least in part on the third integral and the fourth integral.

24. The apparatus of claim 23, wherein the means for calculating a second characterization value comprises:
means for calculating a second ratio comprising the ratio of the fourth integral to the third integral.

25. A computer readable medium storing computer program instructions for characterizing a retinal parameter as a function of polar angle $\theta$, the computer program instructions defining the steps of:
determining an interval of polar angles bounded by a first polar angle and a second polar angle wherein, at each polar angle within the interval, the value of a measurement parameter function is greater than the value of a reference parameter function;
calculating a first integral comprising an integral of the reference parameter function over the interval;
calculating a second integral comprising an integral of the measurement parameter function over the interval; and
calculating a characterization value based at least in part on the first integral and the second integral.

26. The computer readable medium of claim 25, wherein the computer program instructions for calculating a first characterization value comprise computer program instructions defining the step of:
calculating a first ratio comprising the ratio of the second integral to the first integral.

27. The computer readable medium of claim 25, wherein:
the computer program instructions defining the step of calculating a first integral comprise computer program instructions defining the step of calculating:

$$A_L = \int_{\theta_1}^{\theta_2} L(\theta)\,d\theta,$$

wherein $\theta_1$ is the first polar angle, $\theta_2$ is the second polar angle, and $L(\theta)$ is the reference parameter function; and
the computer program instructions defining the step of calculating a second integral comprise computer program instructions defining the step of calculating:

$$A_M = \int_{\theta_1}^{\theta_2} M(\theta)\,d\theta,$$

wherein $M(\theta)$ is the first measurement parameter function.

28. The computer readable medium of claim 27, wherein the computer program instructions for characterizing a retinal parameter as a function of polar angle $\theta$ further comprise computer program instructions defining the step of:
calculating a first ratio $D = A_M/A_L$.

29. The computer readable medium of claim 27, wherein the first measurement parameter function is based at least in part on values of the retinal parameter at a first time.

30. The computer readable medium of claim 29, wherein the computer program instructions for characterizing a retinal parameter as a function of polar angle $\theta$ further comprise computer instructions defining the steps of:
receiving a second measurement parameter function based at least in part on values of the retinal parameter at a second time;
determining a second interval of polar angles bounded by a third polar angle and a fourth polar angle wherein, at each polar angle within the second interval, the value of the second measurement parameter function is less than the value of the reference parameter function;
calculating a third integral comprising an integral of the reference parameter function over the second interval;
calculating a fourth integral comprising an integral of the second measurement parameter function over the second interval; and
calculating a second characterization value based at least in part on the third integral and the fourth integral.

31. The computer readable medium of claim 30, wherein the computer program instructions defining the step of calculating a second characterization value comprise computer program instructions defining the step of:
calculating a second ratio comprising the ratio of the fourth integral to the third integral.

* * * * *

UNITED STATES PATENT AND TRADEMARK OFFICE
CERTIFICATE OF CORRECTION

PATENT NO.        : 8,567,951 B2
APPLICATION NO.   : 13/224568
DATED             : October 29, 2013
INVENTOR(S)       : Yijun Huang et al.

It is certified that error appears in the above-identified patent and that said Letters Patent is hereby corrected as shown below:

In the Claims:

In claim 5, column 11, line 15, "wherein M(θb) is the first measurement" should read --wherein $M(\theta)$ is the first measurement--;

In claim 18, column 12, line 35, "wherein θhd 1 is the first polar angle" should read -- wherein $\theta_1$ is the first polar angle--.

Signed and Sealed this
Ninth Day of September, 2014

Michelle K. Lee
*Deputy Director of the United States Patent and Trademark Office*